(12) United States Patent
Tristan

(10) Patent No.: US 6,997,912 B1
(45) Date of Patent: Feb. 14, 2006

(54) HYPODERMIC NEEDLE COVER ASSEMBLY

(76) Inventor: Andrea Tristan, 255 W. Ansley, San Antonio, TX (US) 78221

( * ) Notice: Subject to any disclaimer, the term of this patent is extended or adjusted under 35 U.S.C. 154(b) by 0 days.

(21) Appl. No.: 10/326,801

(22) Filed: Dec. 19, 2002

Related U.S. Application Data

(60) Provisional application No. 60/342,165, filed on Dec. 19, 2001.

(51) Int. Cl.
*A61M 5/00* (2006.01)
(52) U.S. Cl. .................. 604/263; 604/192; 604/198
(58) Field of Classification Search ........... 604/263, 604/192, 198, 110, 164.08
See application file for complete search history.

(56) References Cited

U.S. PATENT DOCUMENTS

| | | | |
|---|---|---|---|
| 4,982,842 A * | 1/1991 | Hollister | 206/365 |
| 5,055,102 A * | 10/1991 | Sitnik | 604/192 |
| 5,084,027 A * | 1/1992 | Bernard | 604/192 |
| 5,135,509 A * | 8/1992 | Olliffe | 604/192 |
| 5,139,489 A * | 8/1992 | Hollister | 604/192 |
| 5,151,089 A * | 9/1992 | Kirk et al. | 604/192 |
| 5,188,611 A * | 2/1993 | Orgain | 604/192 |
| 5,423,765 A * | 6/1995 | Hollister | 604/192 |
| 5,490,841 A * | 2/1996 | Landis | 604/110 |
| 5,509,907 A * | 4/1996 | Bevilacqua | 604/263 |
| 5,584,816 A * | 12/1996 | Gyure et al. | 604/192 |
| 5,599,318 A * | 2/1997 | Sweeney et al. | 604/263 |
| 5,632,732 A * | 5/1997 | Szabo et al. | 604/192 |
| 5,662,617 A * | 9/1997 | Odell et al. | 604/192 |
| 5,681,295 A * | 10/1997 | Gyure et al. | 604/263 |
| 5,868,716 A * | 2/1999 | Sweeney et al. | 604/263 |
| 6,440,104 B1 * | 8/2002 | Newby et al. | 604/192 |

* cited by examiner

*Primary Examiner*—Sharon Kennedy

(57) ABSTRACT

A hypodermic type needle cover assembly for covering a hypodermic type needle attached to a butterfly needle holding assembly as soon as the tip of the hypodermic type needle is withdrawn form the patient. To ensure the cover remains over the tip of the hypodermic type needle, the cover assembly includes a needle retaining mechanism that allows the needle to easily enter a needle receiving cavity of the cover assembly but provides resistance to the needle moving out of the cover assembly where it could prick and possibly contaminate a health care worker.

16 Claims, 2 Drawing Sheets

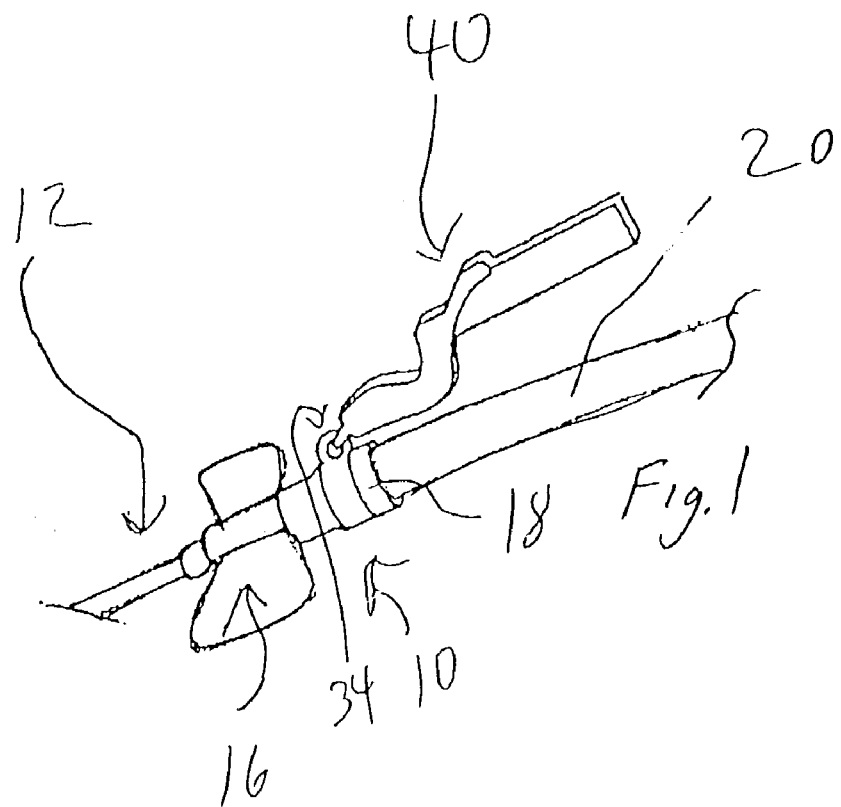
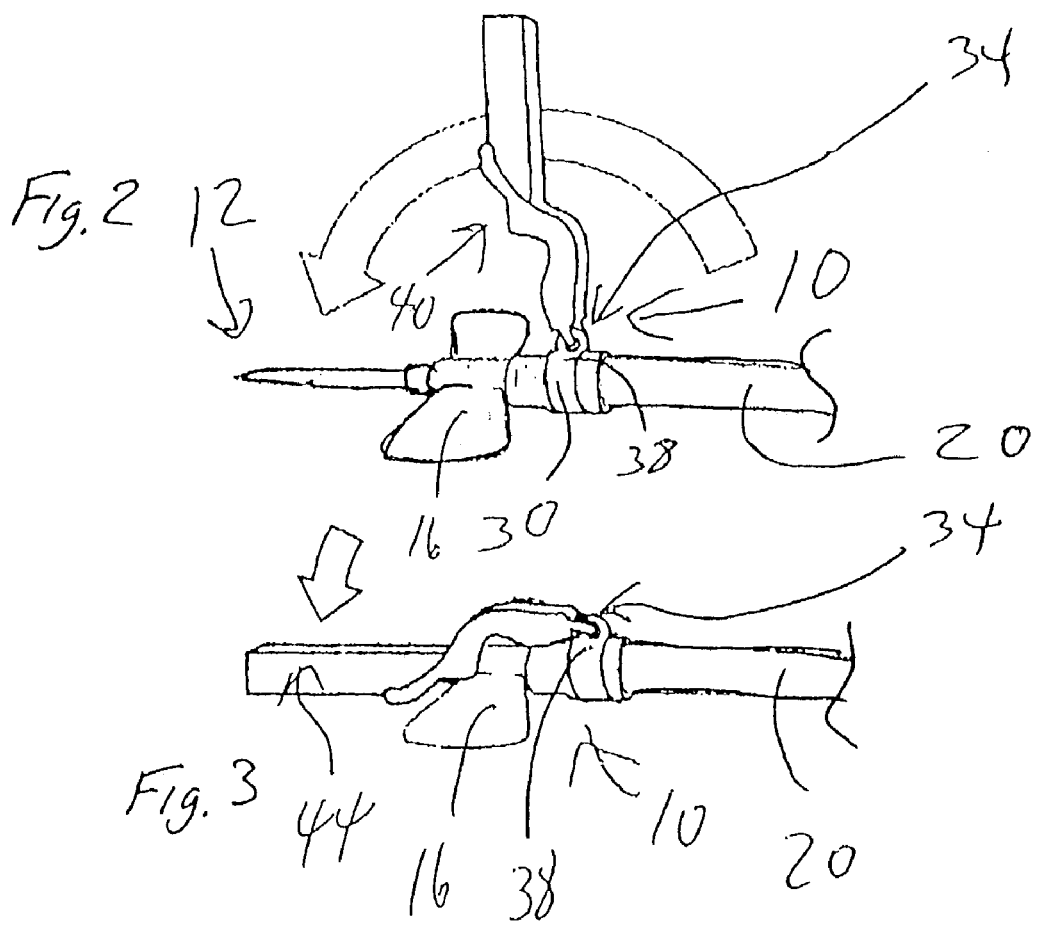

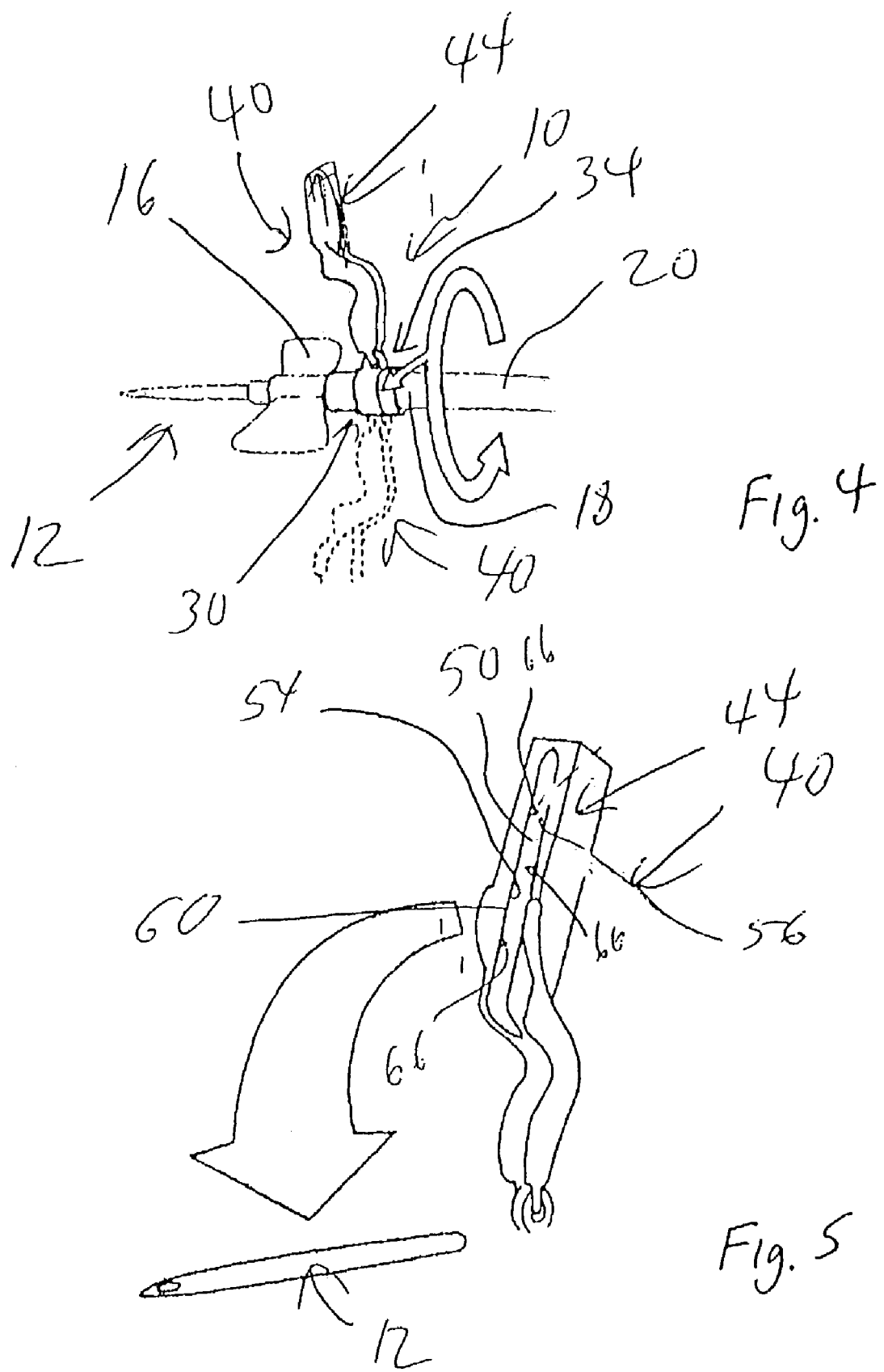

HYPODERMIC NEEDLE COVER ASSEMBLY

This application claims the benefit of 60/342,165 filed on Dec. 19, 2001.

TECHNICAL FIELD

The present invention relates to safety equipment for protecting medical personnel and more particularly to a hypodermic needle cover assembly that is adapted to be used with a hypodermic type needle having a butterfly needle holding assembly having tape sections used for taping the butterfly needle holding assembly to a patient, a first end adapted for connection with a hypodermic type needle and a second end adapted for connection with an end of a length of needle feed tubing; the tape sections holding the hypodermic type needle to a patient while the end of the hypodermic type needle is inserted into a patient; the hypodermic needle cover assembly including a tubular needle feed tube attachment fitting adapted to slip fit over the end of the length of needle feed tubing in connection with the butterfly needle holding assembly on the side of the butterfly needle holding assembly opposite the hypodermic type needle; a hinge assembly provided between a top section of the tubular connection tube attachment fitting and a flipper section having an elongated, open sided, needle cover dimensioned such that the flipper section flips between a storage position away from the hypodermic type needle when an end of the hypodermic type needle is or is about to be inserted into a patient and a cover position wherein the hypodermic type needle is positioned within a needle receiving cavity of the elongated, open sided, needle cover in a manner such that health care workers are protected from being pricked by a contaminated hypodermic type needle after it has been withdrawn from the patient; two opposed sidewalls that partially define the open side of the elongated, open sided, needle cover having a number of resilient needle retaining teeth oriented such that the hypodermic type needle easily passes into the open side and into the needle receiving cavity but is provided resistance from passing out of the open side by the resilient needle retaining teeth; the tubular needle feed tube attachment fitting being rotationally positionable about the end of the length of needle feed tubing.

BACKGROUND ART

Health care providers are at risk of being infected by a needle prick from a blood contaminated needle each time they withdraw a hypodermic type needle from a patient. This is particularly true when the hypodermic type needle is not secured to the end of an elongated, rigid syringe but to a patient attachable structure such as a butterfly needle holding assembly. It would be desirable, therefore, to have a needle cover assembly for covering the hypodermic type needle attached to a butterfly needle holding assembly as soon as the tip of the hypodermic type needle is withdrawn form the patient. To ensure the cover remains over the tip of the hypodermic type needle, it would be a further benefit to have a needle retaining mechanism that allowed the needle to easily enter a needle receiving cavity of the cover but which provided resistance to the needle moving out of the cover where it could prick and possibly contaminate a health care worker.

GENERAL SUMMARY DISCUSSION OF INVENTION

It is thus an object of the invention to provide a hypodermic needle cover assembly that is adapted to be used with a hypodermic type needle having a butterfly needle holding assembly having tape sections used for taping the butterfly needle holding assembly to a patient, a first end adapted for connection with a hypodermic type needle and a second end adapted for connection with an end of a length of needle feed tubing; the tape sections holding the hypodermic type needle to a patient while the end of the hypodermic type needle is inserted into a patient; the hypodermic needle cover assembly including a tubular needle feed tube attachment fitting adapted to slip fit over the end of the length of needle feed tubing in connection with the butterfly needle holding assembly on the side of the butterfly needle holding assembly opposite the hypodermic type needle; a hinge assembly provided between a top section of the tubular connection tube attachment fitting and a flipper section having an elongated, open sided, needle cover dimensioned such that the flipper section flips between a storage position away from the hypodermic type needle when an end of the hypodermic type needle is or is about to be inserted into a patient and a cover position wherein the hypodermic type needle is positioned within a needle receiving cavity of the elongated, open sided, needle cover in a manner such that health care workers are protected from being pricked by a contaminated hypodermic type needle after it has been withdrawn from the patient; two opposed sidewalls that partially define the open side of the elongated, open sided, needle cover having a number of resilient needle retaining teeth oriented such that the hypodermic type needle easily passes into the open side and into the needle receiving cavity but is provided resistance from passing out of the open side by the resilient needle retaining teeth; the tubular needle feed tube attachment fitting being rotationally positionable about the end of the length of needle feed tubing.

Accordingly, a hypodermic needle cover assembly is provided. The hypodermic needle cover assembly is adapted to be used with a hypodermic type needle having a butterfly needle holding assembly having tape sections used for taping the butterfly needle holding assembly to a patient, a first end adapted for connection with a hypodermic type needle and a second end adapted for connection with an end of a length of needle feed tubing; the tape sections holding the hypodermic type needle to a patient while the end of the hypodermic type needle is inserted into a patient; the hypodermic needle cover assembly including a tubular needle feed tube attachment fitting adapted to slip fit over the end of the length of needle feed tubing in connection with the butterfly needle holding assembly on the side of the butterfly needle holding assembly opposite the hypodermic type needle; a hinge assembly provided between a top section of the tubular connection tube attachment fitting and a flipper section having an elongated, open sided, needle cover dimensioned such that the flipper section flips between a storage position away from the hypodermic type needle when an end of the hypodermic type needle is or is about to be inserted into a patient and a cover position wherein the hypodermic type needle is positioned within a needle receiving cavity of the elongated, open sided, needle cover in a manner such that health care workers are protected from being pricked by a contaminated hypodermic type needle after it has been withdrawn from the patient; two opposed sidewalls that partially define the open side of the elongated, open sided, needle cover having a number of resilient needle retaining teeth oriented such that the hypodermic type needle easily passes into the open side and into the needle receiving cavity but is provided resistance from passing out of the open side by the resilient needle retaining teeth; the tubular needle feed tube attachment fitting being rotationally positionable about the end of the length of needle feed tubing.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 1 is a perspective view of a representative hypodermic type needle, a representative butterfly needle holding assembly; a representative end of a length of needle feed tubing; and an exemplary embodiment of the hypodermic needle cover assembly of the present invention with the flipper section flipped into the storage position away from the hypodermic type needle.

FIG. 2 is a perspective view of the representative hypodermic type needle, the representative butterfly needle holding assembly; the representative end of the length of needle feed tubing; and the exemplary embodiment of the hypodermic needle cover assembly of FIG. 1 with the flipper section flipped half way between the storage position away from the hypodermic type needle and the cover position.

FIG. 3 is a perspective view of the representative hypodermic type needle, the representative butterfly needle holding assembly; the representative end of the length of needle feed tubing; and the exemplary embodiment of the hypodermic needle cover assembly of FIG. 1 with the flipper section flipped into the cover position wherein the hypodermic type needle is held within the needle receiving cavity.

FIG. 4 is a perspective view of the hypodermic needle cover assembly showing the tubular needle feed tube attachment fitting being rotationally positionable about the end of the length of needle feed tubing.

FIG. 5 is a perspective, detail view of the hypodermic needle cover assembly showing the open side of the needle cover, the number of resilient needle retaining teeth oriented inward and around the perimeter of the open side such that the hypodermic type needle easily passes into the open side and into the needle receiving cavity of the needle cover assembly but is provided resistance from passing out of the open side by the resilient needle retaining teeth.

EXEMPLARY MODE FOR CARRYING OUT THE INVENTION

FIGS. 1–5 show various aspects of an exemplary embodiment of the hypodermic needle cover assembly of the present invention generally designated 10. Hypodermic needle cover assembly 10 is adapted for use with a hypodermic type needle, generally designated 12, connected to a butterfly needle holding assembly, generally designated 16, and connected to an end 18 of a length of needle feed tubing 20 used for supplying fluids, such as saline or the like, to the needle or drawing fluids out of the patient through the needle 12, such as when the patient is giving blood during a transfusion.

Hypodermic needle cover assembly 10 includes a tubular needle feed tube attachment fitting, generally designated 30, adapted to slip fit over the end 18 of needle feed tubing 20 in connection with the butterfly needle holding assembly 16 on the side of the butterfly needle holding assembly 16 opposite hypodermic type needle 12; a hinge assembly, generally designated 34, provided between a top section 38 of tubular connection tube attachment fitting 30 and a flipper section, generally designated 40, having an elongated, open sided, needle cover, generally designated 44, dimensioned such that the flipper section 40 flips between a storage position away from the hypodermic type needle 12 (shown in FIG. 1) when an end of the hypodermic type needle is or is about to be inserted into a patient and a cover position (shown in FIG. 3) wherein the hypodermic type needle 12 is positioned within a needle receiving cavity 50 of the elongated, open sided, needle cover 44 in a manner such that health care workers are protected from being pricked by a contaminated hypodermic type needle after it has been withdrawn from the patient. Two opposed sidewalls 54,56 that partially define the open side 60 of elongated, open sided, needle cover 44 have a number of inwardly direct, resilient needle retaining teeth 66 oriented such that the hypodermic type needle 12 easily passes into the open side 60 and into the needle receiving cavity 50 but is provided resistance from passing out of the open side 60 by the resilient needle retaining teeth 66.

As shown in FIG. 4, tubular needle feed tube attachment fitting 30 is rotationally positionable about the end 18 of the length of needle feed tubing 20.

It can be seen from the preceding description that a hypodermic needle cover assembly has been provided.

It is noted that the embodiment of the hypodermic needle cover assembly described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A hypodermic needle cover assembly for use with a butterfly type hypodermic needle having a center portion having wing flaps on either side thereof, the hypodermic needle cover assembly comprising:
    a hinge assembly;
    a flipper section;
    the hinge assembly being attached at one end to the wing shaped body of the butterfly type hypodermic needle, said attachment being provided at a location proximal the wing flaps, and at second end to the flipper section;
    the flipper section having an open sided, needle cover dimensioned such that flipper section flips with the hinge assembly between a storage position and a cover position; and
    two opposed sidewalls that at least partially define the open side of the open sided, needle cover.

2. The assembly according to claim 1, wherein the attachment of the hinge assembly to the hypodermic needle is removable.

3. The assembly according to claim 1, wherein the hinge assembly is rotationally positionable.

4. The assembly according to claim 1, wherein the hypodermic needle has a tubular needle feed tube attachment fitting at one end thereof.

5. The assembly according to claim 4, wherein the hinge assembly is attached to a position distal of the tubular needle feed tube attachment fitting.

6. The assembly according to claim 5, wherein the attachment is removable.

7. The assembly according to claim 5, wherein the attachment is rotationally positionable.

8. The assembly according to claim 1, wherein the storage position is a position away from the hypodermic type needle when an end of the hypodermic type needle is about to be inserted into a patient.

9. The assembly according to claim 1, wherein the cover position occurs when hypodermic type needle is positioned within the needle receiving cavity of the elongated, open sided, needle cover manner such that health care workers are protected from being pricked contaminated hypodermic type needle after from the patient.

10. The assembly according to claim 1, wherein the needle receiving cavity comprises a needle retaining device designed to retain the needle in the needle receiving cavity.

11. The assembly according to claim 10, wherein said needle retaining device is at least one needle receiving tooth.

12. The assembly according to claim 11, wherein the needle receiving cavity comprises a plurality of said needle retaining teeth.

13. The assembly according to claim 12, wherein the plurality of needle retaining teeth are oriented inwardly and around at least a portion of the perimeter of the open side such that the needle easily passes into the open side but is resisted from passing out of the open side.

14. The assembly according to claim 13, further comprising a third side wall connecting the two sidewalls at a distal end of the two sidewalls.

15. The assembly according to claim 4, further comprising a length of needle feed tubing.

16. A hypodermic needle cover assembly for use with a butterfly type hypodermic type IV needle having a center portion having wing flaps on either side thereof, a tubular needle feed tube attachment fitting at one end thereof and a wing shaped body from which the pointed tip end of a hypodermic needle extends at the opposite end thereof, the hypodermic needle cover assembly and comprising:

- a hinge assembly;
- a flipper section;
- the hinge assembly being attached at one end to the wing shaped body of the butterfly type hypodermic type IV needle between the IV tubular needle feed tube attachment fitting and the hypodermic needle, said attachment being provided at a location proximal the wing flaps, and at second end to the flipper section;
- the flipper section having an elongated, open sided, needle cover dimensioned such that flipper section flips with the hinge assembly between a storage position away from the hypodermic type needle when an end of the hypodermic type needle is about to be inserted into a patient and a cover position wherein the hypodermic type needle is positioned within a needle receiving cavity the elongated, open sided, needle cover manner such that health care workers are protected from being pricked contaminated hypodermic type needle after from the patient;
- two opposed sidewalls that partially define the open side of the elongated, open sided, needle cover having resilient needle retaining teeth oriented such that the hypodermic number type needle easily passes into receiving cavity but is open side and into the needle provided resistance from passing out of the open side by the resilient needle retaining teeth;
- the tubular needle feed tube attachment fitting being rotationally positionable about the end of the length of needle feed tubing.

* * * * *